United States Patent [19]

Benjamin et al.

[11] Patent Number: 5,399,276

[45] Date of Patent: * Mar. 21, 1995

[54] LUBRICANT COMPOSITION CONTAINING THE REACTION PRODUCT OF AN OLEFINIC COMPOUND AND AN ALKOXYLATED-AMINE-PHOSPHITE

[75] Inventors: Linda A. Benjamin, Horsham, Pa.; Andrew G. Horodysky, Cherry Hill, N.J.; Derek A. Law, Yardley; Shi-Ming Wu, Newtown, both of Pa.

[73] Assignee: Mobil Oil Corporation, Fairfax, Va.

[*] Notice: The portion of the term of this patent subsequent to Dec. 10, 2008 has been disclaimed.

[21] Appl. No.: 685,968

[22] Filed: Apr. 15, 1991

Related U.S. Application Data

[63] Continuation of Ser. No. 385,033, Jul. 26, 1989, abandoned.

[51] Int. Cl.$^6$ ............... C10M 159/12; C10M 137/00
[52] U.S. Cl. .................................................. 252/49.9
[58] Field of Search ........................................ 252/49.9

[56] References Cited

U.S. PATENT DOCUMENTS

| | | | |
|---|---|---|---|
| 2,957,931 | 10/1960 | Hamilton et al. | 252/49.8 |
| 3,105,819 | 10/1963 | Anderson | 252/49.9 |
| 3,202,608 | 8/1965 | Wagenaar | 252/49.9 |
| 4,557,845 | 12/1985 | Horodysky et al. | 252/49.9 |
| 4,657,684 | 4/1987 | Horodysky | 252/49.9 |
| 4,717,491 | 1/1988 | Cardis | 252/46.7 |
| 4,744,912 | 5/1988 | Cardis | 252/46.7 |
| 4,770,800 | 9/1988 | Cardis | 252/46.7 |
| 5,071,577 | 12/1991 | Benjamin et al. | 252/49.9 |
| 5,104,579 | 4/1992 | Benjamin et al. | 252/49.9 |

Primary Examiner—Jerry D. Johnson
Attorney, Agent, or Firm—Alexander J. McKillop; Malcolm D. Keen; Charles A. Malone

[57] ABSTRACT

Alkoxylated- or polyalkoxylate-amine-phosphite derived olefin adducts are superior as lubricating fluid media and as multifunctional additives with internal synergistic antioxidant and extreme pressure/antiwear properties for both mineral and synthetic lubricating oils as well as fuels.

30 Claims, No Drawings

LUBRICANT COMPOSITION CONTAINING THE REACTION PRODUCT OF AN OLEFINIC COMPOUND AND AN ALKOXYLATED-AMINE-PHOSPHITE

This is a continuation of application Ser. No. 07/385,033, filed on Jul. 26, 1989, now abandoned.

BACKGROUND OF THE INVENTION

This invention is directed to hydroxyl-nitrogen-phosphite derived olefinic adducts as multifunctional lubricant additives or as multifuntional fluids or partial replacement fluids having EP/antiwear properties.

The general peroxide catalyzed reaction of dialkyl hydrogen phosphites with conventional olefins to give phosphonate derivatives is known, as disclosed for example, in U.S. Pat. No. 2,957,931. The use of these materials as multifunctional additives in a variety of lubricant applications is also known. These products have demonstrated excellent high and low temperature lubricating properties with exceptional EP/antiwear properties with potential friction reducing and corrosion inhibiting properties.

U.S. Pat. Nos. 4,770,800 and 4,717,491 generally disclose the reaction of dialkyl and trialkyl phosphites with sulfur and thereafter reacting the resultant product with an amine, an olefin or an alkaline oxide to form lube oil products.

U.S. Pat. No. 4,046,774 discloses a method of N-phosphorylating heterocyclic amines to produce products suitable for use as flame retardants.

U.S. Pat. No. 4,744,912 discloses reaction products prepared from sulfurized olefins, dialkyl hydrogen phosphites and primary alkyl amines which are useful for improving lubricant compositions with respect to copper corrosion protection and antiwear protection.

However, no prior art known to applicants disclose hydroxyl-amine-phosphite or hydroxyl nitrogen containing phosphite derived adducts of functionalized and/or polymeric or oligomeric olefins as multifunctional additives as well as multifunctional lubricants with inherent multifaceted internal synergism.

Accordingly it is an object of this invention to provide compositions which exhibit excellent lubricating properties in conjunction with good extreme pressure/antiwear, antioxidant and friction reducing properties.

SUMMARY OF THE INVENTION

The invention is directed to hydroxyl-amine or hydroxyl-nitrogen containing phosphite derived olefin adducts as superior multifunctional and lubricating fluid media with internal synergistic multifunctional antiwear, antioxidant properties and as extreme pressure/antiwear additives for both mineral and synthetic lubricating oils as well as fuels.

Reaction products of polymerized olefin oils such as polyisobutylene, polydecene or polyoctene, or functionalized olefins such as oleyl oleate with various functionalized alkoxylated amine-derived phosphites exhibit excellent lubricating properties in conjunction with good extreme pressure/antiwear antioxidant and friction reducing properties.

The incorporation of the phosphite derivatives onto the backbone of the olefinic oil provides the basis for the unique internal synergistic extreme pressure/antiwear activity, thermal stability and lubricity. Functionalized phosphite-adducts will contribute additional friction reducing, rust inhibiting and hydrolyric stabilizing benefits. All of the above-mentioned properties are believed to be enhanced as a result of this novel multidimensional internal synergism.

The use of these functionalized compositions, as detailed in this application, as lubrication fluids and/or additives in either a mineral or synthetic lubricant is unique and provides unprecedented performance benefits due to the the inherent internal synergism. The process of enhancement of lubricating properties via the addition of these compositions to either mineral or synthetic lubricants is also believed to be unique. For example, the process of improving wear, friction, corrosion inhibition and thermal stability of a polymeric polyisobutylene lubricating oil via the addition of 0.01–100% of an adduct of an alkoxylated amine-derived phosphite and polymeric olefin oils or functionalized olefins, is unique and not reported in prior art. Additionally, the combination of lubricant formulations containing the above compositions with any of the following supplemental additives: dispersants, detergents, viscosity index improvers, EP/antiwear additives, antioxidants, pour depressants, emulsifiers, demulsifiers, corrosion inhibitors, antirust inhibitors, antistaining additives, friction modifiers, and the like is novel.

DETAILED DESCRIPTION OF THE INVENTION

The general peroxide catalyzed reaction of dialkyl hydrogen phosphites with conventional olefins to give phosphonate derivatives is known as disclosed in U.S. Pat. No. 2,957,931. The use of these materials as multifunctional additives in a variety of lubricant applications is also known. These products have demonstrated excellent high and low temperature lubricating properties with exceptional EP/antiwear properties with potential friction reducing and corrosion inhibiting properties.

Incorporation of functionalized phosphites onto the backbone of the polymeric oils such as polyisobutylene or functionalized olefins such as oleyl oleate offers unique advantages over conventional formulated lubricants where volatility or extraction is considered to be important. The products from novel functionalized phosphites with polymeric olefins or functionalized olefins are unique and not evident in prior art.

For example, polymeric or functionalized olefin adducts of alkoxylated amine or polyalkoxylated amine phosphites (I) are expected to improve friction reducing and antiwear performance in addition to rust inhibition. Some heterocyclic substituted alcohol derivatives, e.g. imidazolines (III) and oxazoline (IV) are expected to exhibit antirust, friction reducing and dispersant type properties.

All of the above mentioned olefin-phosphite adducts exhibit beneficial properties from the unique olefin in combination wtih those properties unique to a given functionalized phosphite, and this combination provides for a novel structural class and a unique multifaceted synergistic set of properties. The use of these compositions of matter to improve the above lubricant features either as a functional fluid or partial fluid replacement or as additives for lubricants is believed to be novel.

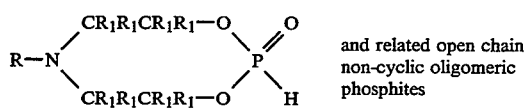

and related open chain non-cyclic oligomeric phosphites (I)

Included in (I) are phosphites derived from the reaction of phosphites with polyalkoxylated amine, such as $R-N[(R_3O)_xH]_2$ or $RNH-(R_3O)_xH$;

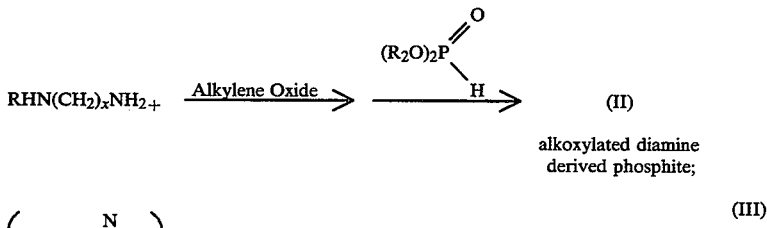

alkoxylated diamine derived phosphite;

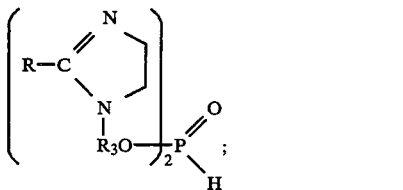 (III)

and

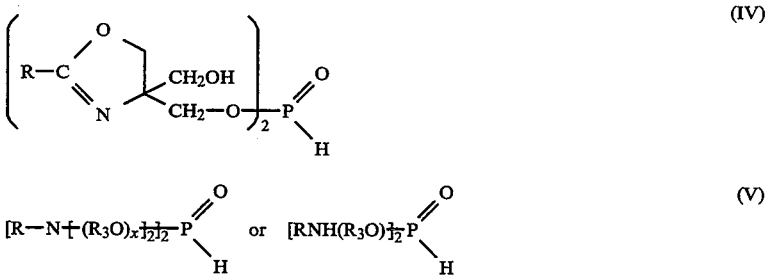

where R is $C_1$ to about $C_{30}$ hydrocarbyl or hydrocarbylene $R_1$ is hydrogen or about $C_1$ to about $C_{30}$ hydrocarbyl or hydrocarbylene $R_2$ is $C_1$ to about $C_{30}$ hydrocarbyl or hydrocarbylene $R_3$ is $C_2$ to about $C_{30}$ hydrocarbyl or hydrocarbylene x is 1 to about 10.

It is to be noted that other structures in addition to structures I to V, set forth above are obtained in the various reactions in accordance with the invention.

The phosphite used can be chosen from one or more of the above structures provided that the phosphite also contains a nitrogen or amine functional group. Such phosphites can be readily obtained as articles of commerce or prepared in any convenient manner known to the art.

The above phosphites can be prepared by the reaction of the hydroxyl containing species with 0.25 to 2 moles of a lower molecular weight dialkyl phosphite such as dimethylphosphite, diethyl phosphite, dibutyl phosphite or the like, heating to approximately 50° C. to 200° C., and performing the transesterification reaction by removal of the lower molecular weight alcohol as it is released during the dialkyl phosphite transesterification reaction.

The preferred olefins are polymeric oils such as polyisobutylene or polypropylene oils containing at least one olefinic linkage. The preferred olefinic oils can contain at least 20 carbon atoms and more preferably contain at least 30 carbon atoms and up to 60 or more carbon atoms and have a MW range of from about 150 to 900. Preferred olefins also include functionalized olefins containing, optionally, sulfur, oxygen, and/or nitrogen such as an olefinic ester as exemplified by oleyl oleate or pentaerythritol tetraoleate. Suitable olefins also include oligomeric decene, oligomeric octene oils and mixtures such as 1-decene trimers, 1-decene tetramers, 1-decene pentamers, 1-octene tetramers, 1-octene pentamers, 1-decene hexamers, 1-decene, 1-decinc decamers, and the like, and mixtures of any of the above olefins. The olefins can also contain one or more hydroxyl groups.

Although generally speaking, preparation of the various reactants, the reaction times, the temperatures and pressures and quantities utilized in the reactions may vary widely and are believed not to be critical. The preferable molar ratio of phosphite to olefinic compound varies from about 1:1 to about 1:2 under ambient conditions of temperature and pressure, although, preferably the reaction temperature is reflux. Temperatures of from 50° C. to 250° C. can be used and the pressure maybe slightly higher than ambient if desired. Sovents can be used if desired. Hydrocarbon solvents such as toluene are preferred.

Reaction catalysts such as peroxides or free radical generating catalysts can significantly aid the reaction. Catalysts include benzoyl peroxides, t-butyl peroxides and the like. Any catalyst capable of generating the appropriate phosphorus free radical can be used to promote the reaction with the olefin.

The additives may be incorporated into any suitable lubricating media or liquid fuel. Suitable lubricating media comprise oils of lubricating viscosity, e.g., mineral or synthetic; or mixtures of mineral and synthetic or greases in which the aforementioned oils are employed as a vehicle or into such functional fluids as hydraulic fluids, brake fluids, power transmission fluids and the like.

In general, mineral oils and/or synthetic oils, employed as the lubricant oil, or grease vehicle may be of any suitable lubricating viscosity range, as for example, from about 45 SSU at 100° F. to about 6000 SSU at 100° F., and, preferably, from about 50 to about 250 SSU at 210° F. These oils may have viscosity indices from below zero to about 100 or higher. Viscosity indices from about 70 to about 95 are preferred. The average molecular weight of these oils may range from about 250 to about 800. Where the lubricant is to be employed in the form of a grease, the lubricating oil is generally employed in an amount sufficient to balance the total grease composition, after accounting for the desired quantity of the thickening agent and other additive components to be included in the grease formulation. When high temperature stability is not a requirement of the finished grease, mineral oils having a viscosity of at least 40 SSU at 150° F., and particularly those falling within the range from about 60 SSU to about 6,000 SSU at 100° F. may be employed.

In instances where synthetic oils are employed as the vehicle for the grease in preference to mineral oils, or in combination therewith, various compounds may be successfully utilized. Typical synthetic vehicles include polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis-(p-phenoxy phenyl) ether, phenoxy phenylethers, etc.

Fully formulated lubricating oils may include in addition to the additives disclosed herein a variety of other additives (for their known purpose) such as dispersants, detergents, inhibitors, antiwear agents, antioxidant, antifoam, pour depressant and other additives including phenates, sulfonates and zinc dithiophosphates.

The lubricating vehicles of the improved greases of the present invention, containing the above described additives, are combined with a grease forming quantity of a thickening agent. For this purpose, a wide variety of materials dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickners may be employed which do not melt and dissolve when used at the required temperature within a particular environment; soap thickeners such as metallic (lithium or calcium) soaps including hydroxy stearate and/or stearate soaps can be used however, in all other respects, any material which is normally employed for thickening or gelling hydrocarbon fluids or forming greases can be used in preparing the aforementioned improved greases in accordance with the present invention.

Included among the preferred thickening agents are those containing at least a portion of alkali metal, alkaline earth metal or amine soaps of hydroxyl-containing fatty acids, fatty glycerides and fatty esters having from 12 to about 30 carbon atoms per molecule. The metals are typified by sodium, lithium, calcium and barium. Preferred is lithium. Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and and soaps of low-, intermediate- and high-molecular weight acids and of nut oil acids.

As has been disclosed hereinabove, the reaction products are useful as multifunctional antiwear/antioxidant-/antirust agents. They are added to the lubricating medium in amounts sufficient to impart such properties to the lubricant. More particularly, such properties will be imparted to the lubricant by adding from about 0.001% to about 10% by weight, preferably from about 0.01% to about 3%, of the neat product.

As mentioned hereinabove, these lubricating additives compositions themselves may be used in amounts up to 100% to provide the lubricating media in its entirety. Thus, the adducts described herein maybe be used in amounts of up to 100% to provide the complete lubricating media or they may be used in amounts less than 100% and with fuels to the extent of from about 5 lbs to about 250 lbs per 1000 bbls. of fuel.

The liquid fuels comtemplated include liquid hydrocarbons, such as gasoline, fuel oils, distillate fuels and diesel oil and liquid alcohols such as methyl alcohol and ethyl alcohol and naphthols and ethers . The fuels also include mixtures of alcohols as well as mixtures of alcohols and liquid hydrocarbons such as gasohol.

Having described the invention in general terms the following examples are exemplary and are not intended to be limitations on the scope of this invention.

EXAMPLES

Example 1

Approximately 74 grams (0.16 mol) of polyisobutene (Indopol L-100) was charged to a stirred reactor equipped with a condenser, thermometer, nitrogen purge inlet and outlet, to which a 30 ml toluene solution of bis(2-hydroxyethyl)oleylamine phosphite (60 grams, 0.08 mol) and di-tert-butyl peroxide (4.0 grams, 3.0 wt %) was added dropwise. At the end of the addition, the reaction mixture was heated to reflux for four hours, then stripped of solvent under vacuum at 130° C. to yield 131 grams of brown fluid.

Example 2

Under the same reaction conditions as described in Example 1, a 20 ml toluene solution of bis(2-hydroxyethyl) oleylamine phosphite (45 grams, 0.06 mol) and di-tert-butyl peroxide (3.3 grams, 3.0 wt %) was added dropwise to oleyl oleate (64 grams, 0.12 mol). The reaction yielded 104.5 grams of light brown fluid after removing volatiles.

Example 3

Under the same reaction conditions as described in Example 1, a 20 ml toluene solution of bis(2-hydroxyethyl)oleylamine phosphite (45 grams, 0.06 mol) and di-tert-butyl peroxide (1.9 grams, 3.0 wt %) was added dropwise to 1-decene (17.5 grams, 0.12 mol). The reaction yielded 54 grams of light brown fluid.

EVALUATION OF PRODUCTS

The products of the above examples were evaluated as lubricant additives at 1.0 wt % concentration in mineral oil. The results were compared to the test oil without additive. These data were obtained on the Four-Ball Wear Apparatus (2000 rpm, 200° F., 60 kg). Test method, ASTM-D-2266, see Table 1, which appears below. For further details of test, see U.S. Pat. No. 4,405,470.

TABLE 1
Four-Ball Wear Test

Wear Factor
$$Kt = \frac{X}{PVT}$$

Kt = Wear Factor (based on thickness change) (express as whole number times 10)
X = Thickness change, in (wear)
P = Contact Pressure, psi
V = Velocity, ft/min
T = Test Duration, h 1.0 wt % additive in mineral based oil (80% solvent paraffinic bright, 20% solvent paraffinic neutral mineral oils)

| | Wear Scar (mm) Diameter | K × 10⁸ K factor |
|---|---|---|
| 0% Additive | 3.89 | 7496 |
| Example 1 | 0.82 | 13.8 |
| Example 2 | 0.57 | 2.74 |
| Example 3 | 0.64 | 4.74 |

The coupling of the polymeric oils or the functionalized olefins with the non-traditional multifunctional phosphite derivatives described in this application leads to novel lubricants and lubricant additives with enhanced oxidative stability, reduced wear, improved rust inhibition and increased load carrying capabilities. In addition, since the phosphite is grafted onto the olefin backbone undesirable properties such as volatility and staining are eliminated. These unique multifunctional adducts have widespread application as additives in either mineral or synthetic base stocks. These materials are economically feasible and can be easily implemented into existing equipment and known technology.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A lubricant composition comprising a major amount of an oil of lubricating viscosity or grease prepared therefrom and a minor amount of a multifunctional antioxidant, friction reducing and extreme pressure/antiwear additive comprising the reaction product of an alkoxylated- or polyalkoxylated-amine-phosphite and an olefinic compound.

2. The composition of claim 1 wherein said alkoxylated amine phosphite has the following generalized structure:

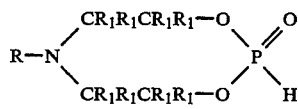

and where R is $C_1$ to about $C_{30}$ hydrocarbyl and $R_1$ is hydrogen or $C_1$ to about $C_{30}$ hydrocarbyl.

3. The composition of claim 1 wherein said alkoxylated amine phosphite is derived from a reaction of phosphites with a polyalkylated amine having one of the following generalized structures:

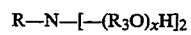

or

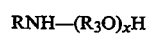

where R is from $C_1$ to about $C_{30}$ hydrocarbyl, $R_3$ is $C_2$ to about $C_{30}$ hydrocarbyl and x is from 1 to about 10.

4. The composition of claim 1 wherein said alkoxylated amine phosphite is derived via the following reaction:

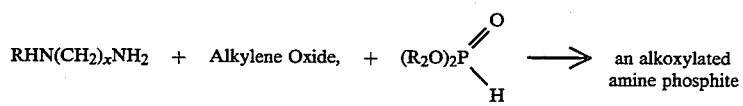

where R is $C_1$ to about $C_{30}$ hydrocarbyl, $R_2$ is $C_1$ to about $C_{30}$ hydrocarbyl and x is from 1 to about 10.

5. The composition of claim 1 wherein said alkoxylated amine phosphite has the following generalized structure:

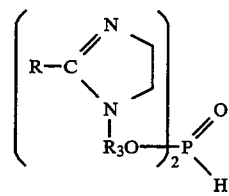

wherein R is from about $C_1$ to about $C_{30}$ hydrocarbyl and $R_3$ is $C_2$ to about $C_{30}$ hydrocarbyl.

6. The composition of claim 1 wherein said alkoxylated amine phosphite has the following generalized structure:

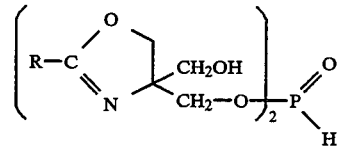

where R is from about $C_1$ to about $C_{30}$ hydrocarbyl.

7. The composition of claim 1 wherein said alkoxylated amine phosphite has the following generalized structure:

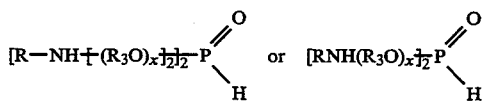

where X is 1 to about 10, where R is $C_1$ to about $C_{30}$ hydrocarbyl and $R_3$ is $C_2$ to about $C_{30}$ hydrocarbyl.

8. The composition of claim 1 wherein said olefinic compound is selected from $C_2$ to about a $C_{60}$ olefin, polymer or oligomer thereof, optionally containing sulfur, oxygen, and/or nitrogen.

9. The composition of claim 8 wherein the olefinic compound is polybutene.

10. The composition of claim 8 wherein said olefinic compound is polydecene.

11. The composition of claim 8 wherein the olefinic compound is polyoctene.

12. The composition of claim 8 wherein the olefinic compound is an olefinic ester.

13. The composition of claim 8 wherein the olefinic compound is a hydroxyl containing olefin.

14. The composition of claim 8 wherein said olefinic compound is an olefin lubricant oil having a viscosity range of from about 45 SSU at 100° F. to about 6000 SSU at 100° F.

15. The composition of claim 1 wherein the alkoxylated amine phosphite is bis(2-hydroxyethyl)oleylamine phosphite.

16. The composition of claim 1 wherein the alkoxylated amine phosphite is bis(2-hydroxyethyl) oleylamine phosphite and said olefinic compound is polyisobutene.

17. The composition of claim 1 wherein the alkoxylated amine phosphite is bis(2-hydroxyethyl) oleylamine phosphite and said olefinic compound is oleyl oleate.

18. The composition of claim 1 wherein the alkoxylated amine phosphite is bis(2-hydroxyethyl) oleylamine phosphite and said olefinic compound is 1-decene.

19. The composition of claim 1 wherein the oil of lubricating viscosity is selected from mineral oils, synthetic oils and mixtures thereof.

20. The composition of claim 19 wherein said oil is a mineral oil.

21. The composition of claim 19 wherein said oil is a synthetic oil.

22. The composition of claim 19 wherein said oil is a mixture of mineral and synthetic oils.

23. The composition of claim 1 wherein said composition is a grease composition.

24. A lubricant composition as claimed in claim 1 containing from about 0.01 to about 10% by weight of the total composition of said multifunctional additive.

25. The composition of claim 1 containing from about 0.5 to about 5 wt % of said multifunctional additive.

26. A process for improving lubricity and the antiwear antioxidant and extreme-pressure properties of a base oil of lubricating viscosity or grease prepared therefrom comprising adding an alkoxylated or polyalkoxylated-amine-phosphite to an olefinic compound and thereafter heating the obtained reaction mixture to reflux for about four hours at a temperature of about 50° C. to about 200° C. at about ambient pressure thereby producing a reaction product and thereafter adding said reaction product to said base oil in an amount of from about 0.001 to less than 100% by weight of the total composition.

27. The process of claim 26 wherein from about 60 to about 90% by weight of the total composition of said product of reaction is added to said oil of lubricating viscosity or grease prepared therefrom.

28. The process of claim 27 wherein said lubricant is selected from mineral oils, synthetic oils or mixtures of mineral oils and synthetic oils.

29. A process for improving the fuel economy of an internal combustion engine comprising contacting the moving parts thereof with the reaction product of an alkoxylated or polyalkoxylated amine phosphite with an olefinic compound which product of reaction is contained in an oil of lubricating viscosity.

30. A lubricant composition comprising an oil of lubricating viscosity or grease prepared therefrom and from about 0.001 wt % to less than 100 wt % of the reaction product of an alkoxylated- or polyalkoxylated-amine-phosphite and an olefinic compound, said reaction product having multi-functional antioxidant friction reducing and extreme pressure/antiwear characteristics.

* * * * *